US006596261B1

(12) United States Patent
Adjei et al.

(10) Patent No.: US 6,596,261 B1
(45) Date of Patent: Jul. 22, 2003

(54) METHOD OF ADMINISTERING A MEDICINAL AEROSOL FORMULATION

(75) Inventors: Akwete L. Adjei, Bridgewater, NJ (US); Simon Stefanos, Morris Plains, NJ (US); Yaping Zhu, Highland Park, NJ (US)

(73) Assignee: Aeropharm Technology Incorporated, Edison, NJ (US)

( * ) Notice: Subject to any disclaimer, the term of this patent is extended or adjusted under 35 U.S.C. 154(b) by 195 days.

(21) Appl. No.: 09/702,194

(22) Filed: Oct. 30, 2000

Related U.S. Application Data

(60) Provisional application No. 60/177,982, filed on Jan. 25, 2000.

(51) Int. Cl.[7] ............................ A61K 9/00; A61K 9/12; A61K 38/00; A61K 38/28

(52) U.S. Cl. ............................... 424/45; 424/43; 514/2; 514/3; 514/12; 514/866; 128/200.14

(58) Field of Search ................ 424/45, 43; 128/200.14; 514/2, 3, 12, 866

(56) References Cited

U.S. PATENT DOCUMENTS 5,889,042 A * 3/1999 MacLean et al. ........... 514/127
6,051,551 A * 4/2000 Hughes et al. ................. 514/3

* cited by examiner

*Primary Examiner*—Michael G. Hartley
*Assistant Examiner*—M. Haghightian
(74) *Attorney, Agent, or Firm*—Frommer Lawrence & HaugLLP

(57) ABSTRACT

A method of treating in a human or animal a condition capable of treatment by oral or nasal inhalation has been found. The method comprises administering a medicinal aerosol formulation comprising a selected medicament under conditions where the amount of the selected drug delivered to the site of action, e.g. the lungs, is maximized.

9 Claims, 2 Drawing Sheets

FIG. 1

Two Compartment Model for Lung Uptake Biotherapeutics

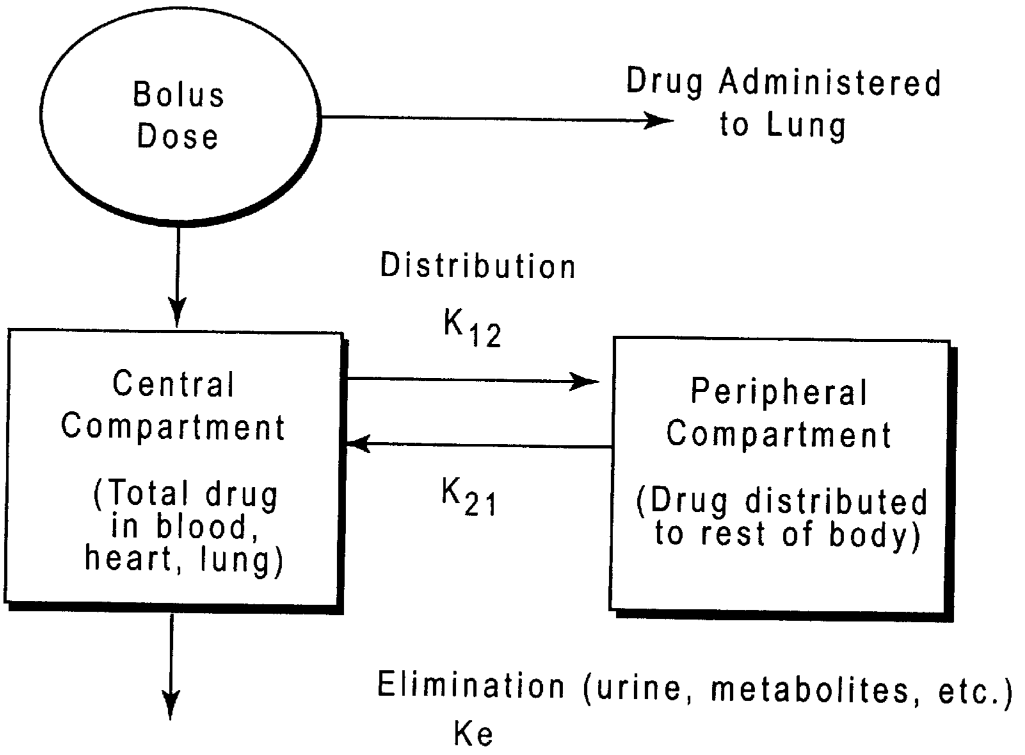

$C = Ae^{-\alpha\tau} + Be^{-\beta\tau}$ (Drug blood concentration at any time, etc.)

Ke = elimination rate constant of drug from the body thru urine $K_{12}$ = rate constant of transfer of drug from blood to other tissues $$\alpha = \frac{K_{21} * Ke}{\beta}$$

$K_{21}$ = rate constant of drug back into blood supply $$\alpha + \beta = K_{12} + K_{21} + Ke$$

$$Ke = \frac{A + B}{\left(\frac{A}{\alpha} + \frac{B}{\beta}\right)}$$

$\alpha + \beta$ = constants

Plasma amylin concentrations following intratracheal aerosol delivery of 7.5μg dose to 6 New Zealand Rabbits

METHOD OF ADMINISTERING A MEDICINAL AEROSOL FORMULATION

This application makes references to U.S. application Ser. No. 09/209,228, filed Dec. 10, 1998, which issued Jul. 17, 2001 as U.S. Pat. No. 6,261,539 B1 and U.S. application Ser. No. 09/158,369, filed Sep. 22, 1998, which issued Oct. 24, 2001 as U.S. Pat. No. 6,136,294, which are incorporated hereinto by reference in their entirety.

BACKGROUND OF THE INVENTION

1. Field of the Invention

This invention relates to a method of administering a medicinal aerosol formulation, and more particularly, to a method of administering a medicinal aerosol formulation where the amount of drug delivered to the lungs of a patent is maximized.

2. Description of the Related Art

Delivery of drugs to the lung by way of inhalation is an important means of treating a variety of conditions, including such common local conditions as cystic fibrosis, pneumonia, bronchial asthma and chronic obstructive pulmonary disease and some systemic conditions, including hormone replacement, pain management, immune deficiency, erythropoiesis, diabetes, etc. Steroids, β agonists, anti-cholinergic agents, proteins and polypeptides are among the drugs that are administered to the lung for such purposes. Such drugs are commonly administered to the lung in the form of an aerosol of particles of respirable size (less than about 10 $\mu$m in diameter). The aerosol formulation can be presented as a liquid or a dry powder. In order to assure proper particle size in a liquid aerosol, particles can be prepared in respirable size and then incorporated into a colloidial dispersion either containing a propellant as a metered dose inhaler (MDI) or air, such as in the case of a dry powder inhaler (DPI). Alternatively, formulations can be prepared in solution form in order to avoid the concern for proper particle size in the formulation. Solution formulations must nevertheless be dispensed in a manner that produces particles or droplets of respirable size.

For MDI application, once prepared an aerosol formulation is filled into an aerosol canister equipped with a metered dose valve. In the hands of the patient the formulation is dispensed via an actuator adapted to direct the dose from the valve to the patient.

What is needed and desired is a method of administering a medicinal aerosol formulation under conditions where a maximum amount of drug contained within the aerosol is delivered to the site to be acted upon, e.g. the lungs.

SUMMARY OF THE INVENTION

A method of treating in a patient a condition capable of treatment by oral or nasal inhalation by administering to the patient an aerosol formulation, comprising a medicament, has been found. In particular, the administration of the medicament is carried out under conditions where the maximum amount of the administered drug is delivered to the site to be acted upon.

BRIEF DESCRIPTION OF THE DRAWING

While the specification concludes with claims particularly pointing out and distinctly claiming the subject invention, it is believed that the following detailed description will be better understood when taken in conjunction with the associated drawings.

FIG. 1 is a schematic drawing upon which the mathematical model of the invention is based.

DETAILED DESCRIPTION OF THE INVENTION

Figure 2:
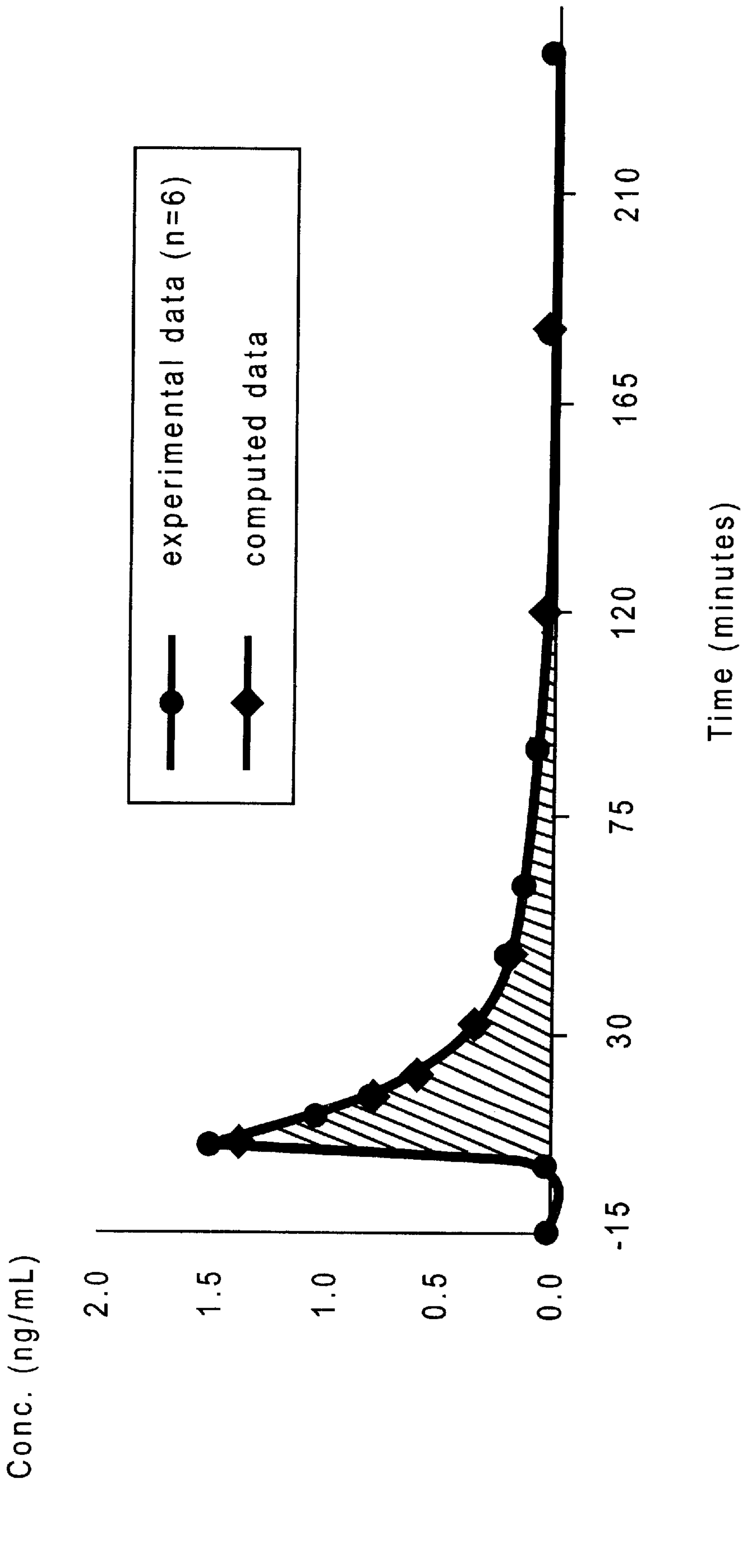
FIG. 2 is a plot of the actual experimental and calculated data for the EXAMPLE.

This application makes reference to U.S. application Ser. No. 09/209,228, filed Dec. 10, 1998 and U.S. application Ser. No. 09/158,369, filed Sep. 22, 1998, which are incorporated hereinto by reference in their entirety.

This invention involves a stable aerosol formulation suitable for delivery which comprises (a) a selected medicament, e.g., a drug for treating diabetes or a condition related thereto, i.e. an anti-diabetic; and (b) a suitable fluid carrier.

A suitable medicament or drug is one which is suitable for administration by inhalation, the inhalation being used for oral and nasal inhalation therapy. Therapeutic categories of drugs or medicaments include antidiabetic agents, e.g. a β-cell hypoglycemic, cardiovascular drugs, antiallergics, analgesics, brochodilators, antihistamines, antitussives, antifungals, antivirals, antibiotics, pain medicaments, antiinflammatories, peptides, proteins and steroids.

Particularly suitable medicaments or drugs include albuterol (also known as salbutamol), atropine, beclomethasone, esters of beclomethasone, such as its monopropionate and dipropionate, budesonide, cromolyn, epinephrine, ephedrine, fentanyl, flunisolide, formoterol, ipratropium bromide, isoproterenol, pirbuterol, prednisolone, triamcinolone acetonide, salmeterol, amiloride, fluticasone esters, such as phosphate, monohydrate and furoate, (−)4-amino-3,5-dichloro-α-[[[6(2-pyridinyl)ethoxy]hexyl]amino]methyl]benzene-methanol. Also included are the suitable acid addition salts of the foregoing drugs, their hydrates and their other solvates. In this regard, suitable acid addition salts include the salts obtained from inorganic acids, such as hydrochloric, hydrobromic, sulfuric, nitric, phosphoric and perchloric acids as well as organic acids such as tartaric, citric, acetic, succinic, maleic, fumaric and oxalic acids. Suitable pharmaceutically acceptable solvates include solvates with ethylactate, alkanes, ethers, alcohols and water.

A suitable β-cell hypoglycemic medicament is one selected from an amylin, an insulin, or any other secretant from β-cells of the pancreas. A suitable synthetic, antidiabetic agent is one selected from an acetohexamide, chlorpropamide, tolazemide, tolbutamide, glipizide, glyburide, glucophage, phentolamine, etc., and a mixture of any two or three of the foregoing medicaments.

A suitable macromolecular medicament or drug is one which is suitable for administration by inhalation, the inhalation being used for oral and nasal inhalation therapy. A stable, colloidal dispersion of a medicament in a fluid, e.g. air, hydrocarbon gases, chlorofluorocarbon (CFC) propellants or non-CFC propellants, such as tetrafluoroethane (HFA-134a) and heptafluoropropane (HFA-227), is described.

A suitable medicament to which the subject invention is directed is one that forms a stable hydrophobic dispersion suitable for delivery to a patient, e.g., human or animal. Typically, the medicament includes a peptide, polypeptide, or protein biotherapeutic ranging from 0.5 K Dalton to 150 K Dalton in molecular size. In particular, the peptide, polypeptide, or protein biotherapeutic medicament includes diabetic aids; insulins and insulin analogs; amylin and amylin analogs such as pramlintide; glucagon; surfactants; immunomodulating peptides such as cytokines, chemokines, lymphokines, interleukins such as taxol, interleukin-1, interleukin-2, and interferons; erythropoetins; thrombolytics and heparins; anti-proteases, antitrypsins and amiloride; rhDNase; antibiotics and other antiinfectives; hormones and growth factors such as parathyroid hormones, LH-RH and GnRH analogs; nucleic acids; DDAVP; calcitonins; cyclosporine; ribavirin; enzymes; heparins; hematopoietic factors; cyclosporins; vaccines; immunoglobulins; vasoactive peptides; antisense agents; genes, oligonucleotides, and nucleotide analogs.

The term diabetic aid includes natural, synthetic, semi-synthetic and recombinant medicaments such as activin, glucagon, insulin, somatostatin, proinsulin, humolin, amylin, and the like.

The term "insulin" shall be interpreted to encompass natural extracted human insulin, recombinantly produced human insulin, insulin extracted from bovine and/or porcine sources, recombinantly produced porcine and bovine insulin and mixtures of any of these insulin products. The term is intended to encompass the polypeptide normally used in the treatment of diabetics in a substantially purified form but encompasses the use of the term in its commercially available pharmaceutical form, which includes additional excipients. The insulin is preferably recombinantly produced and may be dehydrated (completely dried) or in solution.

The terms "insulin analog," "monomeric insulin" and the like are used interchangeably herein and are intended to encompass any form of "insulin" as defined above wherein one or more of the amino acids within the polypeptide chain has been replaced with an alternative amino acid and/or wherein one or more of the amino acids has been deleted or wherein one or more additional amino acids has been added to the polypeptide chain or amino acid sequences which act as insulin in decreasing blood glucose levels. In general, the "insulin analogs" of the present invention include "insulin lispro analogs," as disclosed in U.S. Pat. No. 5,547,929, incorporated hereinto in its entirety by reference, insulin analogs including LysPro insulin and humalog insulin, and other "super insulin analogs", wherein the ability of the insulin analog to affect serum glucose levels is substantially enhanced as compared with conventional insulin as well as hepatoselective insulin analogs which are more active in the liver than in adipose tissue. Preferred analogs are monomeric insulin analogs, which are insulin-like compounds used for the same general purpose as insulin such as insulin lispro i.e., compounds which are administered to reduce blood glucose levels.

The term "immunomodulating proteins" include cytokines, chemokines, complement components, immune system accessory and adhesion molecules and their receptors of human or non-humanannimal specificity. Useful examples include GM-CSF, IL-2, IL-12, OX40, OX40L (gp34), lymphotactin, CD40, CD40L. Useful examples include interleukins for example interleukins 1 to 15, interferons alpha, beta or gamma, tumour necrosis factor, granulocyte-macrophage colony stimulating factor (GM-CSF), macrophage colony stimulating factor (M-CSF), granulocyte colony stimulating factor (G-CSF), chemokines such as neutrophil activating protein (NAP), macrophage chemoattractant and activating factor (MCAF), RANTES, macrophage inflammatory peptides MIP-1a and MIP-1b, complement components and their receptors, or an accessory molecule such as B7.1, B7.2, ICAM-1, 2 or 3 and cytokine receptors. OX40 and OX40-ligand (gp34) are further useful examples of immunomodulatory proteins. Immunomodulatory proteins can for various purposes be of human or non-human animal specificity and can be represented for present purposes, as the case may be and as may be convenient, by extracellular domains and other fragments with the binding activity of the naturally occurring proteins, and muteins thereof, and their fusion proteins with other polypeptide sequences, e.g. with immunoglobulin heavy chain constant domains. Where nucleotide sequences encoding more than one immunomodulating protein are inserted, they can for example comprise more than one cytokine or a combination of cytokines and accessory/adhesion molecules.

The term "interferon" or "IFN" as used herein means the family of highly homologous species-specific proteins that inhibit viral replication and cellular proliferation and modulate immune response. Interferons are grouped into three classes based on their cellular origin and antigenicity, alpha-interferon (leukocytes), beta-interferon (fibroblasts) and gamma-interferon (immunocompetent cells). Recombinant forms and analogs of each group have been developed and are commercially available. Subtypes in each group are based on antigenic/structural characteristics. At least 24 interferon alphas (grouped into subtypes A through H) having distinct amino acid sequences have been identified by isolating and sequencing DNA encoding these peptides. See also Viscomi, 1996 Biotherapy 10:59–86, the contents of which are incorporated by reference hereinto in its entirety. The terms "alpha-interferon", "alpha interferon", "interferon alpha", "human leukocyte interferon" and IFN are used interchangeably herein to describe members of this group. Both naturally occurring and recombinant alpha interferons, including consensus interferon such as that described in U.S. Pat. No. 4,897,471, the contents of which are incorporated hereinto by reference in its entirety, may be used in the practice of the invention. Human leukocyte interferon prepared in this manner contains a mixture of human leukocyte interferons having different amino acid sequences. Purified natural human alpha interferons and mixtures thereof which may be used in the practice of the invention include but are not limited to Sumiferon RTM interferon alpha-n1 available from Sumitomo, Japan; Welfferong interferon alpha-n1 (Ins) available from Glaxo-Wellcome Ltd., London, Great Britain; and Alferon RTM interferon alpha-n3 available from the Purdue Frederick Co., Norwalk, Conn.

The term "erythropoietin" applies to synthetic, semi-synthetic, recombinant, natural, human, monkey, or other animal or microbiological isolated polypeptide products having part or all of the primary structural conformation (i.e., continuous sequence of amino acid residues) and one or more of the biological properties (e.g., immunological properties and in vivo and in vitro biological activity) of naturally-occurring erythropoietin, including allelic variants thereof. These polypeptides are also uniquely characterized by being the product of procaryotic or eucaryotic host expression (e.g., by bacterial, yeast and mammalian cells in culture) of exogenous DNA sequences obtained by genomic or cDNA cloning or by gene synthesis. Products of microbial expression in vertebrate (e.g., mammalian and avian) cells may be further characterized by freedom from association with human proteins or other contaminants which may be associated with erythropoietin in its natural mammalian cellular environment or in extracellular fluids such as plasma or urine. The products of typical yeast (e.g., *Saccaromyces cerevisiae*) or procaryote (e.g., *E. coli*) host cells are free of association with any mammalian proteins. Depending upon the host employed, polypeptides of the invention may be glycosylated with mammalian or other eucaryotic carbohydrates or may be nonglycosylated. Polypeptides of the invention may also include an initial methionine amino acid residue (at position −1). Novel glycoprotein products of the invention include those having a primary structural conformation sufficiently duplicative of that of a naturally-occurring (e.g., human) erythropoietin to allow possession of one or more of the biological properties thereof and having an average carbohydrate composition which differs from that of naturally-occurring (e.g., human) erythropoietin.

The terms "heparins" and "thrombolytics" include anti-clotting factors such as heparin, low molecular weight heparin, tissue plasminogen activator (TPA), urokinase (Abbokinase) prourokinase and other factors used to control clots.

The terms "anti-proteases" and "protease-inhibitors" are used interchangeably and apply to synthetic, semi-synthetic, recombinant, naturally-occurring or non-naturally occurring, soluble or immobilized agents reactive with receptors, or act as antibodies, enzymes or nucleic acids. These include receptors which modulate a humoral immune response, receptors which modulate a cellular immune response (e.g., T-cell receptors) and receptors which modulate a neurological response (e.g., glutamate receptor, glycine receptor, gamma-amino butyric acid (GABA) receptor). These include the cytokine receptors (implicated in arthritis, septic shock, transplant rejection, autoimmune disease and inflammatory diseases), the major histocompatibility (MHC) Class I and II receptors associated with presenting antigen to cytotoxic T-cell receptors and/or T-helper cell receptors (implicated in autoimmune diseases) and the thrombin receptor (implicated in coagulation, cardiovascular disease). The list also includes antibodies which recognize self-antigens such as those antibodies implicated in autoimmune disorders and antibodies which recognize viral (e.g., HIV, herpes simplex virus) and/or microbial antigens.

The terms "hormones" and "growth factors" include hormone releasing hormones such as growth hormone, thyroid hormone, thyroid releasing hormone (TRH), gonadotropin-releasing hormone (GnRH), leuteininzing hormone, leuteininzing hormone-releasing hormone (LH-RH, including the superagonists and antagonists such as leuprolide, deltirelix, gosorelin, nafarelin, danazol, etc.) sourced from natural, human, porcine, bovine, ovine, synthetic, semi-synthetic, or recombinant sources. These also include somatostatin analogs such as octreotide (Sandostatin). Other agents in this category of biotherapeutics include medicaments for uterine contraction (e.g., oxytocin), diuresis (e.g., vasopressin), neutropenia (e.g., GCSF), respiratory disorders (e.g., superoxide dismutase), RDS (e.g., surfactants, optionally including apoproteins), and the like.

The term "enzymes" include recombinant deoxyribonuclease such as DNAse from Genentech, Inc., proteases (e.g., serine proteases such as trypsin and thrombin), polymerases (e.g., RNA polymerases, DNA polymerases), reverse transcriptases and kinases, enzymes implicated in arthritis, osteoporosis, inflammatory diseases, diabetes, allergies, organ transplant rejection, oncogene activation (e.g., dihydrofolate reductase), signal transduction, self-cycle regulation, transcription, DNA replication and repair.

The term "nucleic acids" includes any segment of DNA or RNA containing natural or non-naturally occurring nucleosides, or other proteinoid agents capable of specifically binding to other nucleic acids or oligonucleotides via complementary hydrogen-bonding and also are capable of binding to non-nucleic acid ligates. In this regard, reference is made to Bock, L., et al., Nature 355:564–566 (1992) which reports inhibition of the thrombin-catalyzed conversion of fibrinogen to fibrin using aptamer DNA.

Examples of biological molecules for which lead molecules can be synthesized and selected in accordance with the invention include, but are not limited to, agonists and antagonists for cell membrane receptors, neurotransmitters, toxins and venoms, viral epitopes, hormones, opiates, steroids, peptides, enzyme substrates and inhibitors, cofactors, drugs, lectins, sugars, oligonucleotides, nucleic acids, oligosaccharides, lipids, proteins, and analogs of any of the foregoing molecules.

The term "analog" refers to a molecule, which shares a common functional activity with the molecule to which it is deemed to be an analog and typically shares common structural features as well.

The term "recombinant" refers to any type of genetically engineered molecule, or combinatorial library of molecules which may be further processed into another state to form a second combinatorial library, especially molecules that contain protecting groups which enhance the physicochemical, pharmacological, and clinical safety of the biotherapeutic agent.

The term "vaccine" refers to therapeutic compositions for stimulating cellular immune responses, either isolated, or through an antigen presenting cell, such as an activated dendritic cell, that is able to activate T-cells to produce a multivalent cellular immune response against a selected antigen. The potent antigen presenting cell is stimulated by exposing the cell in vitro to a polypeptide complex. The polypeptide complex may comprise a dendritic cell-binding protein and a polypeptide antigen, but preferably, the polypeptide antigen is either a tissue-specific tumor antigen or an oncogene gene product. However, it is appreciated that other antigens, such as viral antigens can be used in such combination to produce immunostimulatory responses. In another preferred embodiment, the dendritic cell-binding protein that forms part of the immunostimulatory polypeptide complex is GM-CSF. In a further preferred embodiment, the polypeptide antigen that forms part of the complex is the tumor-specific antigen prostatic acid phosphatase. In still other preferred embodiments, the polypeptide antigen may be any one of the oncogene product peptide antigens. The polypeptide complex may also contain, between the dendritic cell-binding protein and the polypeptide antigen, a linker peptide. The polypeptide complex may comprise a dendritic cell-binding protein covalently linked to a polypeptide antigen, such polypeptide complex being preferably formed from a dendritic cell binding protein, preferably GM-CSF, and a polypeptide antigen. The polypeptide antigen is preferably a tissue-specific tumor antigen such as prostatic acid phosphatase (PAP), or an oncogene product, such as Her2, p21RAS, and p53; however, other embodiments, such as viral antigens, are also within the contemplation of the invention.

The term "immunoglobulins" encompasses polypeptide oligonucleotides involved in host defense mechanisms such as coding and encoding by one or more gene vectors, conjugating various binding moieties of nucleic acids in host defense cells, or coupling expressed vectors to aid in the treatment of a human or animal subject. The medicaments included in this class of polypeptides include IgG, IgE, IgM, IgD, either individually or in a combination with one another.

The term "amylin" includes natural human amylin, bovine, porcine, rat, rabbit amylin, as well as synthetic, semi-synthetic or recombinant amylin or amylin analogs including pramlintide and other amylin agonists as disclosed in U.S. Pat. No. 5,686,411, and U.S. Pat. No. 5,854,215, both of which are incorporated hereinto by reference in their entirety.

For purposes of the formulations of this invention, which are intended for inhalation into the lungs, the selected medicament or drug is preferably micronized whereby a therapeutically effective amount or fraction (e.g. ninety percent or more) of the medicament is particulate. Typically, the particles have a diameter of less than about 10 microns, and preferably less than about 5 microns, in order that the particles can be inhaled into the respiratory tract and/or lungs.

The particulate medicament or drug is present in the inventive formulations in a therapeutically effective amount, that is, an amount such that the drug can be administered as a dispersion or an aerosol, such as topically, or via oral or nasal inhalation, and cause its desired therapeutic effect, typically preferred with one dose, or through several doses. The selected drug or medicament, e.g. particulate β-cell hypoglycemic medicament or insulin, is administered as an aerosol from a conventional valve, e.g., a metered dose valve, through an aerosol adapter also known as an actuator.

The term "amount" as used herein refers to quantity or to concentration as appropriate to the context. The amount of the selected drug, e.g. the β-cell hypoglycemic medicament or mixture of medicaments, that constitutes a therapeutically effective amount varies according to factors such as the potency of the particular medicament or drug, e.g. insulin, or drugs used, the route of administration of the formulation, and the mechanical system used to administer the formulation. A therapeutically effective amount of a particular drug or drugs can be selected by those of ordinary skill in the art with due consideration of such factors. Generally a therapeutically effective amount will be from about 0.001 parts by weight to about 5 parts by weight based on 100 parts by weight of the fluid carrier e.g. propellant.

A suitable fluid carrier is selected. A suitable fluid carrier includes air, a hydrocarbon, such as n-butane, propane, isopentane, etc. or a propellant. A suitable propellant is any fluorocarbon, e.g. a 1–6 hydrogen containing flurocarbon such as $CHF_2CHF_2$, $CF_3CH_2F$, $CH_2F_2CH_3$ and CF3CHFCF3, a perfluorocarbon, e.g. a 1–4 carbon perfluorocarbon, such as $CF_3CF_3$, $CF_3CF_2CF_3$; or any mixture of the foregoing, having a sufficient vapor pressure to render them effective as propellants. Some typical suitable propellants include conventional chlorofluorocarbon (CFC) propellants such as propellants 11, 12 and 114 or a mixture of any of the foregoing propellants. Non-CFC propellants such as 1,1,1,2-tetrafluoroethane (Propellant 134a), 1,1,1,2,3,3,3-heptafluoropropane (Propellant 227) or mixtures thereof are preferred. The propellant is preferably present in an amount sufficient to propel a plurality of the selected doses of the drug from an aerosol canister.

Optionally, a suitable stabilizer is selected. A suitable stabilizer is a "water addition". As used herein a "water addition" is an amount of water which (1) is added, either initially with other components of the aerosol formulation, e.g. medicament and fluid carrier, or after the other components, e.g. medicament, fluid carrier, are combined and processed, (2) is in addition to the water which is always present and which develops during processing and/or storage of the aerosol formulation, i.e. "developed" or "nascent" formulation water, and (3) is present in an amount which further stabilizes a medicinal aerosol formulation having nascent formulation water.

An aerosol formulation preferably comprises the water addition in an amount effective to more effectively stabilize the formulation relative to an identical formulation not containing the water addition, i.e. containing only nascent formulation water, such that the drug does not settle, cream or flocculate after agitation so quickly as to prevent reproducible dosing of the drug. Reproducible dosing can be achieved if the formulation retains a substantially uniform drug concentration for about fifteen seconds to about five minutes after agitation.

The particular amount of the water addition that constitutes an effective amount is dependent upon the particular fluid carrier, e.g. propellant, and on the particular drug or drugs used in the formulation. It is therefore not practical to enumerate specific effective amounts for use with specific formulations of the invention, but such amounts can readily be determined by those skilled in the art with due consideration of the factors set forth above. Generally, however, the water addition must be present in a formulation in an amount in excess of the concentration of the nascent formulation water. Such concentration of nascent formulation water typically ranges up to 300 parts by weight per one million parts by weight of the total weight of the aerosol formulation. Accordingly, the water addition in excess of this nascent water concentration typically ranges from about 10 parts by weight to 5000 parts by weight per one million parts by weight of the total aerosol formulation weight. Most preferred is that the concentration of the water addition in excess of this nascent water concentration is from 500 parts by weight to 5000 parts by weight per one million parts by weight of the total weight of the medicinal aerosol formulation.

It is to be emphasized that this is an amount which exceeds the amount of nascent or developed formulation water. It is also to be stressed that preferably this amount of water addition can be added and initially combined with the other components of the formulation, e.g. an amylin, glucogan and fluid carrier, e.g. 1,1,1,2-tetrahydrofluoroethane. However, the water addition can be added to the resultant formulation after these other components have been processed, e.g. prior to or subsequent to storage.

It has surprisingly been found that the formulation of the invention is stable without the necessity of employing a cosolvent, such as ethanol, or surfactants. However, further components, such as conventional lubricants or surfactants, cosolvents, ethanol, etc., can also be present in an aerosol formulation of the invention in suitable amounts readily determined by those skilled in the art. In this regard, reference is made to U.S. Pat. No. 5,225,183, which is incorporated by reference hereinto in its entirety. Typically, a co-solvent, such as ethanol, is added in an amount ranging from about 0.5 to about 10% by weight of the total weight of the formulation.

A most preferred formulation comprises the medicament, the fluid carrier, the ethanol cosolvent and the water addition, for example, an amylin, 1,1,1,2-tetrafluoroethane, ethanol and the water addition.

Generally the formulations of the invention can be prepared by combining (i) the selected drug or drugs in an amount sufficient to provide a plurality of therapeutically effective doses; (ii) the fluid, e.g. propellant, in an amount sufficient to propel a plurality of doses, e.g. from an aerosol canister; (iii) optionally, the water addition in an amount effective to further stabilize each of the formulations; and (iv) any further optional components, e.g. ethanol as a cosolvent; and dispersing the components. The components can be dispersed using a conventional mixer or homogenizer, by shaking, or by ultrasonic energy as well as by the use of a bead mill or a microfluidizer. Bulk formulations can be transferred to smaller individual aerosol vials by using valve to valve transfer methods, pressure filling or by using conventional cold-fill methods. It is not required that a component used in a suspension aerosol formulation be soluble in the fluid carrier, e.g. propellant. Components that are not sufficiently soluble can be coated or congealed with polymeric, dissolution controlling agents in an appropriate amount and the coated particles can then be incorporated in a formulation as described above. Polymeric dissolution controlling agents suitable for use in this invention include, but not limited to polylactide glycolide co-polymer, acrylic esters, polyamidoamines, substituted or unsubstituted cellulose derivatives, and other naturally derived carbohydrate and polysaccharide products such as zein and chitosan.

Where a macromolecular medicament is employed, optionally a suitable second stabilizer is selected. A suitable second stabilizer is a protective colloid and includes (1) an amino acid selected from (a) a monoamino carboxylic acid of the formula, $H_2N—R—COOH$ (I), (b) a monoamino dicarboxylic acid of the formula, $H_2N—R(COOH)_2$ (II) and (c) a diamino monocarboxylic acid of the formula $(H_2N)_2—R\ COOH$ (III), where R is a straight or branched alkyl radical of from 1 to 22 carbon atoms, which can be mono or poly-substituted with moieties such as sulfide (—S—), oxide (—O—), hydroxyl (—OH), amide (—NH), sulfate (—SO4); aryl of the formula

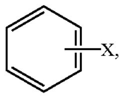

where X is hydrogen, halogen (F, Cl, BR, I), alkyl of 1 to 6 carbon atoms, alkoxy of 1 to 6 carbon atoms, hydroxy and nitro; and heterocyclic, such as thienyl, furyl, pyranyl, imidazolyl, pyrrolyl, thizolyl, oxazolyl, pyridyl, and pyrimidinyl compounds; (2) a derivative of the amino acid selected from (a) acid addition salts of the amino group, obtained from inorganic acids, such as hydrochloric, hydrobromic, sulfuric, nitric, phosphoric, and perchloric acids, as well as organic acids, such as tartaric, citric, acetic, succinic, maleic, fumaric, oxalic acids; (b) amides of the carboxylic acid group, e.g., glutamine, di-peptides, e.g. salts and esters of oxidized and unoxidized L-cysteinylglycine, gamma-L-glutamyl-L-cysteine, N-acetyl-L-cysteine-glycine, either conjugated, unconjugated or polymeric forms of L-Gly-L-Glu and L-Val-L-Thr, L-aspartyl-L-phenylalanine, muramyl dipeptides, nutrients such as L-tyrosyl-L-tyrosine, L-alanyl-L-tyrosine, L-arginyl-L-tyrosine, L-tyrosyl-L-arginine, N-Cbz-L-Leu-L-Leu-OCH and its salts or esters, glycyl-glycine, N-acetyl-L-aspartate-L-glutamate (NAAG), etc.; and tripeptides, e.g. oxidized and unoxidized gamma-L-glutamyl-L-cysteinylglycine; muramyl tripeptides, etc. (c) esters of the carboxylic acid group obtained from aliphatic straight or branched chain alcohols of from 1 to 6 carbon atoms, e.g. L-aspartyl-L-phenylalanine methylester (Aspartame®), (3) an ether of any of the foregoing; (4) a hydrate or semi-hydrate of any of the foregoing and (5) a mixture of the amino acid and the derivative of the amino acid.

Suitable amino acids of the formula I include glycin, glycine, alanine, valine, leucine, isoleucine, leucylalanine, methionine, threonine, isovaline, phenylalanine, tyrosine, serine, cysteine, N-acetyl-L-cysteine, histidine, tryptophan, proline, and hydroxyproline, e.g. trans-4-hydroxy proline. Compounds of the formula II include, aspartic acid, and glutamic acid, compounds of the formula (III) include arginine, glutamine, lysine, hydroxylysine, ornithine, asparagine, and citrulline.

A fluid or aerosol formulation preferably comprises the protective colloid stabilizer in an amount effective to stabilize the formulation relative to an identical formulation not containing the stabilizer, such that the drug does not settle, cream or flocculate after agitation so quickly as to prevent reproducible dosing of the drug. Reproducible dosing can be achieved if the formulation retains a substantially uniform drug concentration for about fifteen seconds to about five minutes after agitation.

Typically, for optimal functional and therapeutic performance of the aerosol formulation, either as a dry powder or as an aerosol suspension, the stabilizer is present either as a coarse carrier (e.g., 20–90 $\mu$m) or as a finely micronized powder, $\leqq 10\ \mu$m in diameter. In either case, reproducible drug dosimetry is obtained without the need to qualify the inspiratory maneuver of the patient. Accordingly, excellent dose uniformity is obtained at tidal flows of up to 2 liters, or at inspiratory flow rates of as low as 15 liters per minute to about 90 liters per minute.

The particular amount of stabilizer that constitutes an effective amount is dependent upon the particular stabilizer, the particular propellant, and on the particular drug used in the formulation. It is therefore not practical to enumerate specific effective amounts for use with specific formulations of the invention, but such amounts can readily be determined by those skilled in the art with due consideration of the factors set forth above. Generally, however, the protective colloid stabilizer can be present in a formulation in an amount from about 0.0001 parts per million to about 200, 000 parts per million, more preferably about 1 part per million to about 10,000 parts per million, most preferably from about 10 parts per million to about 5,000 parts per million of the total formulation.

Aerosol canisters equipped with conventional valves, preferably metered dose valves, can be used to deliver the formulations of the invention. It has been found, however, that selection of appropriate valve assemblies for use with aerosol formulations is dependent upon the particular component and other adjuvants used (if any), on the fluid, e.g. propellant, and on the particular drug being used. Conventional neoprene and buna valve rubbers used in metered dose valves for delivering conventional CFC formulations often have less than optimal valve delivery characteristics and ease of operation when used with formulations containing HFC-134a or HFC-227. Therefore certain formulations of the invention are preferably dispensed via a valve assembly wherein the diaphragm is made of a nitrile rubber such as DB-218 (American Gasket and Rubber, Schiller Park, Ill.) or an EPDM rubber such as Vistalon™ (Exxon), Royalene™ (UniRoyal), bunaEP (Bayer). Also suitable are diaphragms fashioned by extrusion, injection, molding or compression molding from a thermoplastic elastomeric material, such as FLEXOMER™ GERS 1085 NT polyolefin (Union Carbide).

Conventional aerosol canisters, coated or uncoated, anodized or unanodized, e.g., those of aluminum, glass, stainless steel, polybutyl or polyethylene terephthalate, and coated canisters or cans with epon, epoxy, etc., can be used to contain a formulation of the invention.

The formulation of the invention can be delivered to the respiratory tract and/or lung by oral inhalation in order to treat diabetes and a diabetes related condition susceptible of treatment by inhalation. The formulations of the invention can also be delivered by nasal inhalation in order to treat, e.g., diabetes (systemic), or they can be delivered via oral (e.g., buccal) administration in order to treat, e.g., diabetes and a diabetes related condition.

A mathematical model has been developed for the optimal delivery of the formulations of the invention to the lungs of an animal or human being treated. The model is based upon the schematic drawing contained in FIG. 1.

Referring to FIG. 1, when a formulation of the invention is administered to a patient, e.g., an animal or human being, via an aerosol dosage spray to the lung of such patient, the total amount of the administered drug, e.g. an insulin, an amylin, etc., enters the blood stream of the patient (designated as the "Central Compartment"). All or part of the drug may then be removed from the blood (central compartment) of the patient by natural elimination, e.g. in the urine, from the body of the patient at a rate constant designated as "Ke". Alternatively, all or part of the drug may be distributed (metabolism and excretion) from the central compartment (blood, heart) of the patient to the rest of the body, e.g. lymph, muscle, skin, kidney, of such patient (designated as the "Peripheral Compartment"), at a constant rate of transfer designated as "$K_{12}$". Concurrently with the transfer to the Peripheral Compartment there is a return of the drug therefrom to the Central Compartment at a rate constant of transfer designated as "$K_{21}$". Of course the amount destined to be transferred back to the Central Compartment may go partially or completely to elimination at the rate constant Ke or go to the Peripheral Compartment at rate $K_{12}$ maybe or maybe not followed by transmittal at rate $K_{21}$.

In the mathematical model for optimal delivery via an aerosol of a formulation of the invention, the designations or symbols are defined as follows:

$\alpha$ is a constant;

$\beta$ is a constant;

C is the concentration of the drug in the Central Compartment, e.g. blood, at any time ("t")

A is a constant; and

B is a constant.

The critical determination is the volume of distribution of the central compartment ("Vc") which defines the effectiveness and stability of the drug administered to the lung of the patient being treated and defines the perfusion of the administered drug in the body. The Vc basically is a number which defines the area of the body, i.e. site of action, e.g. the lungs, kidney, liver, muscle which the administered drug reaches and affects or covers. Vc is calculated as follows, where $$Vc = \frac{D}{A+B}, \quad \text{(I)}$$

where, $$Ke = \frac{A+B}{\left(\frac{A}{\alpha} + \frac{B}{\beta}\right)}, \quad \text{(II)}$$

$$A = \frac{D(K_{21} - \alpha)}{Vc(\beta - \alpha)} \quad \text{(III)}$$

-continued $$B = \frac{D(K_{21} - \beta)}{Vc(\alpha - \beta)} \quad \text{(IV)}$$

$$\alpha + \beta = K_{12} + K_{21} + Ke \quad \text{(V); and}$$

$$C = Ae^{-\alpha t} + Be^{-\beta t} \quad \text{(VI).}$$

EXAMPLE

Six New Zealand rabbits having an average weight in the range of 2.5 to 4 kg were treated intravenously with a 5.0 mg/kg dose of amylin and compared to six other rabbits who were given a dose of 7.5 mg/kg of amylin by intrapulmonary administration. The table listed below discloses the average measured results

TABLE 1

| | Intravenous Administration (dose: 5.0 $\mu$g/kg) | Intrapulmonary Administration (dose: 7.5 $\mu$g/kg) |
|---|---|---|
| Vd (liters) | 9.5246 | 63.0911 |
| K12 (minutes$^{-1}$) | 0.0180 | 0.03211 |
| K21 (minutes$^{-1}$) | 0.0075 | 0.01774 |
| Ke (minutes$^{-1}$) | 0.0403 | 0.02627 |
| *T1/2 (minutes) | 17.1771 | 26.3819 |
| **AUC (ng/mL.minute) | 45.4016 | 16.9670 |
| ***F (Bioavalability) | — | 24.9% |

*Half life of the drug in the body
**Area under the blood concentration time course curve of FIG. 2
***Percent of administered drug absorbed from the lung dose.

Referring to FIG. 2, the experimental results obtained were compared to the results calculated using formulae (I) through (VI). The calculated data is totally consistent with the experimental data of this EXAMPLE.

We claim:

1. A method to treating in a human or an animal a condition treated by oral or nasal inhalation, which comprises, administering an aerosol formulation comprising a medicament for the condition to said human or animal by oral or nasal inhalation, under conditions where the volume of distribution, Vc, is the maximum value; where $$Vc = \frac{D}{A+B}$$

$$Ke = \frac{A+B}{\left(\frac{A}{\alpha} + \frac{B}{\beta}\right)},$$

$$\alpha + \beta = K_{12} + K_{21} + Ke, \text{ and}$$

$$C = Ae^{-\alpha t} + Be^{-\beta t}$$

where Ke is the rate constant of elimination of said medicament from the blood of said human or animal; $K_{12}$ is the rate constant of transfer of said medicament from the blood of said human or animal to the rest of the body of said human or animal, $K_{21}$ is the rate constant of the return of said medicament to the blood of said human or animal, $\alpha$ and $\beta$ are constants, C is the concentration of said medicament in the blood of said human or animal at any time, A is constant, B is constant and D is the dose of said administered medicament.

2. The method as defined in claim 1 wherein said medicament is selected from the group consisting of albuterol, atropine, beclomethasone, beclomethasone monopropionate, beclomethasone dipropionate, budesonide, cromolyn, epinephrine, ephedrine, fentanyl, flunisolide, formoterol, ipratropium bromide, isoproterenol, pirbuterol, prednisone, triamcinolone acetonide, salmeterol, amiloride, fluticasone, fluticasone esters, (−)4-amino-3,5-dichloro-α-[[[6(2-pyridinyl)ethoxy]hexyl]amino]methyl]benzene-methanol and pharmaceutically acceptable salts, esters, hydrates and solvates of the foregoing.

3. The method as defined in claim 1 wherein said medicament is a protein or peptide medicament having a molecular size ranging from about 1 K Dalton to about 150 K Daltons.

4. The method as defined in claim 3, wherein said medicament is selected from the group consisting of an insulin, amylin, glacagon, LH-RH, deltirex, leuprolide, gosorelin, nafarelin, octreotide, somatostatin, calcitonin, porathyroid hormone, TRH, growth hormone-releasing hormone, G-CSF, G-SF, a cytokine, rhDNAse, heparin, an antibiotic, albumin, ovalbumin, aminloride, DDAVP, VIP, a cyclosporin, erthropoietin, inteferon, IgG, IgE, IgM, IgA, IgD, interleukin, IRAP, papain DNAse, peroxidase, serratio peptidase, antityrpsin, catalase, α-1-antitrypsin, ribavirin or a mixture of any of the foregoing medicaments.

5. The method as defined in claim 3, wherein said medicament is selected from the group consisting of an insulin, amylin, glucagon, LH-RH, deltirex, leuprolide, gosorelin, nafarelin, octreotide, somatostatin, calcitonin, porathyroid hormone, TRH, growth hormone-releasing hormone, G-CSF, G-SF, a cytokine, rhDNAse, heparin, an antibiotic, albumin, ovalbumin, aminloride, DDAVP, VIP, a cyclosporin, erthropoietin, inteferon, IgG, IgE, IgM, IgA, IgD, interleukin, IRAP, papain DNAse, peroxidase, serratio peptidase, antityrpsin, catalase, α-1-antitrypsin, a gene, a vector, an oligonucleotide, ribavirin or a mixture of any of the foregoing medicaments.

6. The method as defined in claim 1 wherein said medicament is an antidiabetic agent.

7. The method as defined in claim 6 wherein said antidiabetic agent is selected from the group consisting of acetohexamide, chlorpropamide, tolazemide, tolbutamide, glipizide, glyburide, glucophage, phentolamine and any mixture of the foregoing agents.

8. A method of maximizing the delivery of a medicament to the lungs of a human or other animal patient in need of such medicament delivery, which comprises:

(a) treating the patient with the medicament by nasal or oral propellant inhalation with an aerosol formulation of the medicament; and (b) maintaining the volume distribution, Vc, of said medicament aerosol at a maximum value, where $$Vc = \frac{D}{A+B}$$

$$Ke = \frac{A+B}{\left(\frac{A}{\alpha} + \frac{B}{\beta}\right)},$$

$\alpha+\beta=K_{12}+K_{21}+Ke$, and $C=Ae^{-\alpha t}+Be^{-\beta t}$ where Ke is the rate constant of elimination of said medicament from the blood of said human or animal; $K_{12}$ is the rate constant of elimination of said medicament from the blood of said human or animal; $K_{12}$ is the rate constant of transfer of said medicament from the blood of said human or animal to the rest of the body of said human or animal, $K_{21}$ is the rate constant of the return of said medicament to the blood of said human or animal, α and β are constants, C is the concentration of said medicament in the blood of said human or animal at any time, A is constant, B is constant and D is the dose of said medicament.

9. A method to treating a condition in a human or an animal, which comprises, administering an aerosol formulation comprising a medicament for the condition to said human or animal by oral or nasal inhalation, under conditions where the volume of distribution, Vc, is the maximum value; where $$Vc = \frac{\text{dose of said administered medicament}}{A+B}$$

$$Ke = \frac{A+B}{\left(\frac{A}{\alpha} + \frac{B}{\beta}\right)},$$

$\alpha+\beta=K_{12}+K_{21}+Ke$, and $C=Ae^{-\alpha t}+Be^{-\beta t}$ where Ke is the rate constant of elimination of said medicament from the blood of said human or animal; $K_{12}$ is the rate constant of transfer of said medicament from the blood of said human or animal to the rest of the body of said human or animal, $K_{21}$ is the rate constant of the return of said medicament to the blood of said human or α and β are constants, C is the concentration of said medicament in the blood of said human or animal at any time, A is constant, and B is constant.

* * * * *

UNITED STATES PATENT AND TRADEMARK OFFICE

CERTIFICATE OF CORRECTION

PATENT NO. : 6,596,261 B1
DATED : July 22, 2003
INVENTOR(S) : Adjei et al.

It is certified that error appears in the above-identified patent and that said Letters Patent is hereby corrected as shown below:

Column 12,
Line 38, the term "to" should be deleted and replaced with the term -- for --.

Column 14,
Line 24, the term "to" should be deleted and replaced with the term -- for --.
Line 47, "human or" should be deleted and repaced with -- human or animal --.

Signed and Sealed this

Twenty-first Day of June, 2005

JON W. DUDAS
*Director of the United States Patent and Trademark Office*